United States Patent [19]

Knifton

[11] 4,013,583

[45] Mar. 22, 1977

[54] PROCESSES FOR REGENERATING DISPERSIONS OF LIGAND STABILIZED, PALLADIUM AND PLATINUM (II) HALIDE-COMPLEXES USED IN CARBONYLATION AND HYDROFORMYLATION CATALYSTS

[75] Inventor: John F. Knifton, Poughquag, N.Y.

[73] Assignee: Texaco Inc., New York, N.Y.

[22] Filed: May 27, 1975

[21] Appl. No.: 581,395

[52] U.S. Cl. .................... 252/415; 252/413; 252/429 R; 260/410.9 R; 260/429 R; 260/429.7; 260/468 M; 260/497 R; 260/514 M; 260/515 R; 260/533 A; 260/604 HF; 260/666 R; 260/676 R

[51] Int. Cl.² .................. B01J 31/40; B01J 27/32; C07C 51/00; C11C 3/02

[58] Field of Search ...... 252/415, 413, 414, 429 R; 260/410.9 R, 413, 533 A

[56] References Cited

UNITED STATES PATENTS

| | | | |
|---|---|---|---|
| 3,420,873 | 1/1969 | Olivier | 252/415 |
| 3,455,989 | 7/1969 | Kutepow et al. | 260/514 M |
| 3,641,076 | 2/1972 | Booth | 260/429 R |
| 3,700,706 | 10/1972 | Butter | 260/410.9 R |
| 3,832,391 | 8/1974 | Parshall | 260/413 |

*Primary Examiner*—Patrick P. Garvin
*Assistant Examiner*—P. E. Konopka
*Attorney, Agent, or Firm*—T. H. Whaley; C. G. Ries; Bernard Marlowe

[57] ABSTRACT

This invention concerns using mineral acid treatment for the regeneration of carbonylation and hydroformylation catalysts consisting of dispersions of ligand-stabilized palladium(II) and platinum(II) halide complexes in quaternary ammonium, phosphonium and arsonium salts of trihalostannate(II) and trihalogermanate(II).

3 Claims, No Drawings

PROCESSES FOR REGENERATING DISPERSIONS OF LIGAND STABILIZED, PALLADIUM AND PLATINUM (II) HALIDE-COMPLEXES USED IN CARBONYLATION AND HYDROFORMYLATION CATALYSTS

STATEMENT OF THE INVENTION

This invention pertains to the art of regenerating spent noble metal catalyst complexes useful for the carbonylation, hydroformylation and hydrogenation of olefins.

More particularly, this invention concerns the regeneration of certain carbonylation and hydroformylation catalysts consisting of dispersions of ligand-stabilized palladium(II) and platinum(II) halide complexes in quaternary ammonium, phosphonium and arsonium salts of trihalostannate(II) and trihalogermanate(II).

A. BACKGROUND OF THE INVENTION

This invention concerns a process for regenerating certain noble metal catalysts used in the carbonylation, hydroformylation and hydrogenation of olefins. Carbonylation refers here to the reaction of an olefin with carbon monoxide and an active-hydrogen-containing compound selected from the group consisting of an alkanol or water. This reaction is exemplified in eq. 1, wherein $R_1$, $R_2$, $R_3$ and $R_4$, individually, are hydrogen, alkyl up to 12 carbon atoms, alkenyl of up to 12 carbon atoms, or aryl up to 12 carbon atoms, or mixed alkyaryl or arylalkyl groups.

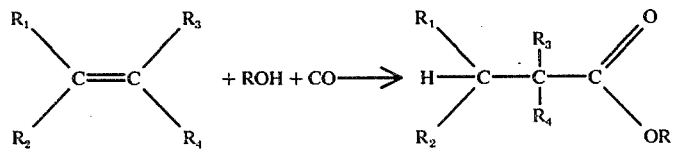

Suitable alkanols (ROH) include primary and secondary alcohols of 1 to 12 carbons, phenols, substituted alcohols and polyols. The major products of carbonylation are fatty (carboxylic) acids and their esters.

Hydroformylation is conducted by the reaction of a mixture of olefin, carbon monoxide and hydrogen, in the presence of a suitable catalyst. The process of hydroformylation may be expressed by eq. 2, wherein $R_1$, $R_2$, $R_3$ and $R_4$ are defined as above. The major products are aldehydes or alcohols.

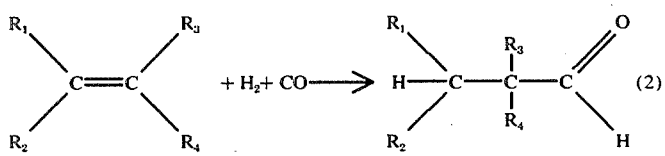

The preparation of the fatty acids or fatty esters using metal carbonyls or carbonyl precursons to catalyze the carbonylation of olefins (eq. 1) is old in the literature, originally involving Reppe and his coworkers and contemporaries. Reviews by C. W. Bird [Chem Rev. 62, 283 (1962)] document this work. Unfortunately, many of these carbonyl-type catalysts have the disadvantages of inherent toxicity, they require stringent reaction conditions which in turn lead to competing side reactions such as olefin isomerization, polymerization and reduction, and they exhibit poor selectivity to the desired linear acid ester.

Recently, more acceptable homogeneous catalyst systems have been developed which offer substantially improved selectivity in converting olefins to primarily linear fatty acids or linear fatty esters, in good yield, under moderate reaction conditions of temperature and pressure.

As is usually the case, after much more extensive usage, certain drawbacks have become more evident. These include difficulty in maintaining high conversions, high selectivities and high yields after recycling the catalyst several times. These problems are due to catalyst degradation as well as catalyst decomposition, mechanical losses and further catalyst decomposition during the separation of the products from the homogeneous catalysts and the inert solvents of the reaction mixture. Thermal instability of the catalyst is particularly troublesome in the recovery and working-up of certain ligand-stabilized homogeneous palladium catalyst reaction mixtures.

In order to avoid or minimize these problems, the use of molten quaternary ammonium, phosphonium and arsonium salts of trihalostannate(II) and trihalogermanate(II) as both solvent and part of the catalytic entity has been disclosed, particularly in the two U.S. Pat. Nos. of G. W. Parshall, 3,657,368 and 3,565,823 which are believed to be the closest known art except for applicant's more recently filed Ser. No. 526,867 filed 11/25/74 in the U.S. Patent Office.

However, in order to develop a commercially acceptable regeneration catalytic process it is necessary to demonstrate several key positive advantages:

1. A simple and efficient means of separating catalyst from the products,
2. The ability to recycle the catalyst without its substantial deactivation. This is particularly important in the case of the thermally sensitive palladium catalysts.
3. Regeneration processes which are capable of restoring the activity of the deactivated catalyst, particularly at high concentrations of catalysts up to 0.1 mole % concentration in the feed.

In this application are disclosed two different illustrative procedures for isolating organic products such as are produced by olefin carbonylation, hydroformylation and hydrogenation. These organic products may be separated in high purity from the palladium and platinum catalysts consisting of dispersions of ligand-stabilized palladium(II) halide and platinum(II) halides in quaternary ammonium, phosphonium and arsonium salts of trihalostannate(II) and trihalogermanate(II) by the procedures disclosed infra, and the palladium or platinum catalysts recycled with fresh olefin feed. The most important aspect of this application is the claimed process for restoring the activity of the above mentioned spent catalyst dispersions of the palladium(II) or platinum salts in quaternary ammonium, phosphonium and arsonium salts of trihalostannate(II) and trihalogermanate(II) by the treatment described below.

B. RECYCLING PROCESSES FOR PALLADIUM CARBONYLATION CATALYSTS, SUCH AS ARE DISCLOSED IN SER. NO. 526,867

While the claims of the inventive regeneration process are primarily directed to the regeneration of spent catalysts obtained by carbonylation, hydroformylation or hydrogenation process utilizing dispersions of platinum(II) or palladium(II) halides dispersed in quaternary ammonium, phosphonium or arsonium salts of trihalostannate(II) and trihalogermanate(II), in fact the inventive process can be employed to regenerate spent catalysts from unrelated processes. After the termination of the preparative process, many other isolation procedures can be used. Two isolation processes have been illustrated. In the first case, the product typified by an ester, is isolated by solvent extraction with a solvent such as petroleum ether. This extraction procedure (Procedure I) is as described below.

a. Separate the crude product liquid from the solid catalyst by filtration or decantation.

b. Distill the liquid product under atmospheric pressure or less (1 cm to 75 cm Hg.) to strip off unreacted olefin and alkanol.

c. Treat the liquid residue from step (b) with a suitable organic solvent, such as petroleum ether, so as to extract the product fatty acid ester fraction into the solvent phase, and precipitate any dissolved catalyst melt.

d. Fractionally distill the organic solvent extract from step (c) under reduced pressure (1 mm to 75 cm Hg.) to recover fatty acid ester products.

e. Combine the recovered solid catalyst from steps (a) and (c), and recycle with additional olefin and alkanol, and CO under pressure.

The solvents employed in the inventive process of Procedure I, part c, to isolate the catalyst from the ester products are not critical as to volume or type. For convenience sake about 0.1 parts by volume to $10^3$ parts by volume of organic solvent is employed for each part by volume of catalyst. Suitable organic solvents include among others: paraffinic solvents such as petroleum ethers, heptane, hexane and n-octane etc., chlorinated solvents such as o-dichlorobenzene, chloronaphthalene etc., nitrocompounds including nitrobenzene, o-nitroanisole, p-nitroanisole nitromethane and 2-nitropropane, ketones such as methyl isobutyl ketone, acetone and methyl ethyl ketone, sulphones such as dimethylsulfone as well as dimethylsulfoxides, ethers such as diethyl ether, aromatics such as benzene, toluene and xylenes, acetonitrile and related compounds, and mixtures thereof.

This procedure for product ester recovery is illustrated in Example 1, described infra.

A second, alternative, method of separating the organic products, such as esters, from the solid catalyst involves a distillation procedure, as follows.

a. Separate the crude product from the solid catalyst by filtration or decantation.

b. Distill the liquid product under atmospheric pressure or less (1 cm to 75 cm Hg.) to recover unreacted olefin and alkanol.

c. Fractionally distill the residual liquid from step (b) under reduced pressure (1 mm to 75 cm Hg.) to recover fatty acid ester product.

d. Combine the recovered solid catalyst from steps (a) and (c), add additional olefin and alkanol, and recycle the reaction mix with CO under pressure.

This procedure for product ester recovery is illustrated in Examples 2 and 3, described infra.

EXAMPLE 1

PREPARATION OF METHYL NONANOATE WITH RECOVERY BY SOLVENT EXTRACTION

To a degassed sample of 1-octene (400 mmole) and methanol (30 ml.) contained in a 300 cc reactor equipped for pressurizing, heating, cooling and means of agitation is added under a nitrogen environment, tetraethylammonium trichlorostannate(II) (42 mmole) and bis(triphenylphosphine) palladium(II) chloride (4.4 mmole). The reactor is sealed, deoxygenated with a purge of nitrogen, and pressurized under carbon monoxide (1500 psig) while heating the agitated mixture between 80° and 90° C for 3–10 hours. At the end of this time the reaction is terminated by cooling and venting the reactor. The crude liquid product (79 ml.) is filtered to remove solid palladium catalyst, rotary evaporated at 40°–60° C under 2–20 cm Hg. pressure, and extracted with 200 ml. of petroleum ether in three portions. The combined ether extracts are distilled at 40° C (2–60 cm Hg.), and the methyl nonanoates recovered as residual liquid (60 ml. purity 95%).

The recovered 18.1 g of palladium catalyst from the above experiment is charged to a second degassed sample of 1-octene (400 mmole) and methanol (30 ml.), and the mixture carbonylated as described supra. The methyl nonanoate ester is recovered by solvent extraction as above, the solid palladium catalyst is then recycled with two additional batches of fresh 1-octene, methanol mixture. A summary of the octene conversion, and methyl nonanoate selectivity and yield data for the four catalyst cycles is given in Table 1. Gas chromatographic analyses were used to determine the conversion and selectivity data.

TABLE 1

| PALLADIUM CARBONYLATION CATALYST RECYCLE STUDIES - METHYL NONANOATE SYNTHESIS | | | | | |
|---|---|---|---|---|---|
| EXAMPLE 1: | MELT COMPOSITION: [(C$_2$H$_5$)$_4$N][SnCl$_3$]-PdCl$_2$[P(C$_6$H$_5$)$_3$]$_2$ | | | | |
| | Cycle | Octene Conv (%) | Methyl Nonanoates$^c$ Selectivity(%)$^d$ Yield(Mole %)$^e$ | | Isolated Ester Purity (%) | Total Liquid Yield (%) |
| | I$^a$ | 80 | 86.3 | 85 | 95 | 85 |
| | II | 80 | 86.5 | 81 | 95 | 88 |
| | III | 74 | 89.5 | 72 | 96 | 94 |
| | IV | 29 | 90.6 | 25 | 98 | 96 |
| EXAMPLE 2: | | | | | | |
| | I$^b$ | 80 | 83.1 | 82 | 99 | 90 |

TABLE 1-continued
PALLADIUM CARBONYLATION CATALYST RECYCLE STUDIES - METHYL NONANOATE SYNTHESIS MELT COMPOSITION: $[(C_2H_5)_4N][SnCl_3]\text{-}PdCl_2[P(C_6H_5)_3]_2$

| | | | | | |
|---|---|---|---|---|---|
| II | 61 | 89.3 | 61 | 99 | 91 |
| III | N.D. | 89.0 | 60 | 99 | 90 |
| IV | 32 | 87.8 | 28 | 99 | 87 |

[a]Run Conditions: 85° C, 1500 psig. CO, 10 hr., [Sn]/[Pd]=9.6, initial [1-octene]/[Pd]=92, [CH₃OH]/[1-octene]=1.9
[b]Run Conditions: 85° C, 1500 psig. CO, 8 hr.,[Sn]/[Pd]=10, initial [1-octene]/[Pd]=100, [CH₃OH]/[1-octene]=1.9
[c]A mixture of methyl nonanoate with some methyl 2-methyl octanoate and methyl 2-ethylheptanoate.
[d]Selectivity to linear methyl nonanoate based on total methyl nonanoate/total methyl C₉ ester.
[e]Yield based on octene charged.

EXAMPLE 2
PREPARATION OF METHYL NONANOATE WITH RECOVERY BY DISTALLATION

To a degassed sample of 1-octene (400 mmole) and methanol (30 ml.) contained in a reactor equipped for pressurizing, heating, cooling, and means of agitation is added under a nitrogen environment, tetraethylammonium trichlorostannate(II) (40 mmole) and bis(triphenylphosphine)-palladium(II) chloride (4.0 mmole). The reactor is sealed, deoxygenated with a purge of nitrogen, and pressured under carbon monoxide (1500 psig) while heating the agitated mixture between 80° and 90° C for 3-8 hours. At the end of this time, the reacton is terminated by cooling and venting the reactor. The crude liquid product (83 ml.) is recovered by decantation, rotary evaporated at 40°-60° C under 2-10 cm Hg. pressure, and the residual liquid fractionally distilled at 1-3 mm Hg. pressure. The fraction distilling at 48°-51° C is identified by nmr, ir, glpc and elemental analyses as methyl nonanoates (60 ml., purity >99%).

The recovered solid palladium catalyst from the above experiment is charged to a second degassed sample of 1-octene (400 mmole) and methanol (30 ml.), and the mixture carbonylated as described supra. On cooling, the methyl nonanoate ester is recovered by the distillation procedure described, and the palladium catalyst is then recycled with two further batches of fresh 1-octene, methanol mixture. A summary of the octene conversion, and methyl nonanoate selectivity and yield data for the four catalyst cycles is given in Table 1.

EXAMPLE 3
PREPARATION OF ETHYL NONANOATE WITH RECOVERY BY DISTILLATION

Using the same general procedure as described in Example 2, additional runs are made with 1-octene, ethanol mixture and two samples of the catalyst system:

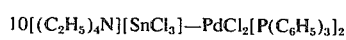

A total of ten batches of 1-octene, ethanol mixture were carbonylated by the procedure of Example 2, five batches for each catalyst sample. The purpose was to determine the degree of reproducibility of the palladium catalyst for ethyl nonanoate synthesis. The data are summarized in Table 2, some conclusions are as follows:

a. While olefin conversions and nonanoate ester yields remain essentially the same over the first three cycles, catalyst deactivation evidently starts to have a substantial deterrent on product yield in subsequent cycles.

b. Selectivity to be linear nonanoate ester improves steadily with successive recycling.

c. Samples of the palladium catalyst show good reproducibility. The yield data in Table 2 for the two catalyst samples agree within ∓2% for cycle 1, and the standard deviation after the 5th cycle is only 7.8%. Variations in linear fatty acid ester selectivity within each cycle are never greater than ∓3%, and are below 1% on the 5th cycle.

d. Storage stability of the catalysts is also good. A sample of recovered catalyst from the second cycle shows good activity even after storage in air for 10 days.

e. The purity of the isolated ethyl nonanoates (determined by glpc) remains essentially constant over 5 cycles at >99%.

TABLE 2
PALLADIUM CATALYST REPRODUCIBILITY STUDIES - ETHYL NONANOATE SYNTHESIS[a]

CATALYST COMPOSITION: $[(C_2H_5)_4N][SnCl_3]\text{-}PdCl_2[P(C_6H_5)_3]_2$

| CATALYST: Ethyl C₉ Ester | Cycle 1 | | Cycle 2 | | Cycle 3 | | Cycle 4 | | Cycle 5 | |
|---|---|---|---|---|---|---|---|---|---|---|
| | Sample 1 | Sample 2 | Sample 1 | Sample 2 | Sample 1 | Sample 2 | Sample 1 | Sample 2 | Sample 1 | Sample 2 |
| Linearity (%) | 69.9 | 68.1 | 78.3 | 84.3 | 87.7 | 89.8 | 89.5 | 91.4 | 91.4 | 90.9 |
| Yield by G.C. (Mole %) | 84 | 88 | 86 | 85 | 81 | 62 | 79 | 45 | 15 | 26 |
| Yield Isolated (Mole %) | 79 | 78 | 77 | 76 | 71 | 51 | 67 | 31 | 11 | 19 |
| Purity (%) | >99 | >99 | >99 | >99 | >99 | >99 | >99 | >99 | >99 | >99 |
| Liquid Yield (%) | 93 | 90 | 97 | 99 | 100 | 99 | 100 | 100 | 100 | 100 |

[a]Run at 85°, 1500 psig. CO, 8 hr., [Sb]/[Pd]=10, [1-octene]/[Pd]=63, [C₂H₅OH]/[1-octene]=1.0

C. REGENERATION OF PALLADIUM CARBONYLATION CATALYSTS

The regeneration of deactivated dispersions of ligand-stabilized palladium(II) halide in quaternary ammonium, phosphonium and arsonium salts of trihalostannate(II) or trihalogermanate(II) may be carried out by various techniques. A method that has been successfully applied to fatty acid ester synthesis is described in the following examples. Examples 4 and 5 deal with the regeneration of spent palladium catalyst by treatment with mineral acid. In the experimental work of Examples 4 and 5, a 1-octene, ethanol mixture is carbonylated by the procedure described in Example 2, and the ethyl nonanoate product ester recovered by distillation. After 3 to 6 cycles of the catalyst, the latter is regenerated by mineral acid treatment as follows:

a. The recovered catalyst sample consisting essentially of a dispersion of ligand-stabilized palladium(II) halide in quaternary ammonium, phosphonium and arsonium salts of trihalostannate(II) or trihalogermanate(II) is treated with mineral acid, consisting of a mixture of hydrochloric and nitric acids.

b. The mixture of solid catalyst plus acid is evaporated to a solid at 50°–110° C.

c. Additional stabilizing ligand, such as triphenylphosphine, is added to the recovered solid catalyst from step (b) in the proportion of 1 to 10 moles of ligand per mole of palladium.

d. The regenerated catalyst is washed with excess solvent mixture, filtered and dried in vacuo.

The mineral acid employed to regenerate said spent dispersions of palladium carbonylation catalyst is not critical as to volume, composition or specific gravity. For convenience sake, about 0.1 parts by weight to $10^3$ parts by weight of mineral acid is employed for each part by weight of catalyst. The mineral acid normally consists of a mixture of hydrochloric acid (specific gravity 1.00 to 1.20 at 20° C) and nitric acid (specific gravity 1.00 to 1.51 at 20° C) in volume ratios ranging from 0.01 to 100 parts by volume of hydrochloric acid for each part by volume of nitric acid.

The organic solvent used to wash the regenerated catalyst in step (d), after mineral acid treatment, is preferably an equivolume mixture of olefin plus alkanol, the olefin and alkanol being preferably those selected for subsequent carbonylation steps. For example, in a series of syntheses of ethyl nonanoate, the regenerated catalyst is refluxed with a mixture of 1-octene and ethanol. Other organic solvents may also be used to reflux the mineral acid treated catalyst in step (d) however, including paraffinic solvents such as petroleum ethers, heptane, hexane etc., chlorinated solvents such as o-dichlorobenzene, chloronaphthalene, carbon tetrachloride, chloroform, dichloromethane, etc., nitrocompounds including nitrobenzene, o-dinitroanisole, nitromesitylene, nitromethane and 2-nitropropane, ketones such as acetone, methyl isobutyl ketone, and methyl ethyl ketone, sulfones such as dimethylsulfone as well as dimethylsulfoxides, ethers such as diethyl ether, aromatics like benzene, toluene and xylenes, acetonitrile, and mixtures thereof.

EXAMPLE 4

PALLADIUM CATALYST REGENERATION VIA MINERAL ACID TREATMENT

Using the general carbonylation procedure of Example 2, a liquid mix of degassed 1-octene (0.5 mole) and ethanol (0.5 mole), together with the catalyst components tetraethylammonium trichlorostannate(II) (80 mmole) and bis(triphenylphosphine)palladium(II) chloride (8.0 mmole), are charged to a 300 ml. glass-lined reactor, purged with $N_2$, and pressuring with CO (1500 psig) while heating to 80°–90° C for 3–8 hours. Carbonylation is terminated by cooling and venting the reactor. The crude product liquid (78–108 ml.) is recovered by decantation, rotary evaporated at 40°–60° under 2–10 cm Hg. pressure, and the residual liquid fractionally distilled at 1–3 mm Hg. pressure. The fraction distilling at 70°–75° C is identified as ethyl nonanoates (50–90 ml., purity >99%) by nmr, ir, glpc and elemental analyses.

The recovered solid palladium catalyst is charged to a second degassed sample of 1-octene (0.5 mole) and ethanol (0.5 mole), and the mixture carbonylated as described supra. On cooling, the ethyl nonanoate esters are recovered by the distillation procedure described, and the palladium catalyst is then recycled with two additional batches of fresh 1-octene, ethanol mixture.

After 4 cycles, the 35 gm of recovered solid palladium catalyst is treated with 30 ml. of 1:1 (v/v) conc. hydrochloric acid (specific gravity 1.19 at 20° C) and nitric acid (specific gravity 1.42 at 20° C). The solid, liquid mixture is evaporated to dryness at 70°–95° C and the residual solids treated in a similar manner with two additional quantities of concentrated hydrochloric acid (20 ml. each) at 70°–95° C. The brown-colored recovered solid is then treated with triphenylphosphine (16 mmole) and washed with 1:1 ethanol/octene (100 ml.). After drying in vacuo, the regenerated palladium catalyst is ready for recycle with fresh 1-octene (0.5 mole), ethanol (0.5 mole) as described supra. Regeneration of the catalyst is repeated after the 9th cycle. A summary of the octene conversion and ethyl nonanoate selectivity and yield data for a thirteen cycle experiment is given in Table 3.

TABLE 3

| | PALLADIUM CATALYST REGENERATION VIA MINERAL ACID TREATMENT - ETHYL NONANOATE SYNTHESIS[a] | | | | | |
|---|---|---|---|---|---|---|
| Cycle | Octane Conv(%) | Ester Linearity (Mole %) | Ethyl Nonanoate Yield (Mole %) By G.C. | Isolated | Isolated Ester Purity (%) | Total Liquid Yield (%) |
| I | 91 | 67.3 | 77 | 63 | 99 | 83 |
| II | 78 | 71.8 | 77 | 68 | 99 | 93 |
| III | 62 | 86.6 | 56 | 46 | 99 | 98 |
| IV | 40 | 90.8 | 47 | 33 | 99 | 98 |
| V | 46 | 86.6 | 44 | 28 | 98 | 92 |
| VI | 59 | 86.3 | 71 | 46 | 99 | 96 |
| VII | 64 | 81.7 | 79 | 58 | 99 | 98 |
| VIII | 44 | 86.2 | 57 | 43 | 99 | 92 |
| IX | 9.8 | 88.8 | 9.0 | 7.4 | 99 | 90 |
| X | 3 | 89.8 | 1.9 | N.D. | — | 89 |
| XI | 61 | 83.6 | 65 | 50 | 99 | 100 |
| XII | 43 | 85.6 | 44 | 41 | 99 | 89 |
| XIII | 4.6 | 86.6 | 4.2 | N.D. | — | 100 |

[a]Run conditions: 85°, 1500 psig. CO, 6–8 hr., initial [1-octene]/[Pd]=50, [Sn]/[Pd]=10, [ethanol]/[1-octene]=1.5 1.0

It may be noted that in this experimental series the performance of the catalyst after regeneration by mineral acid appears comparable with fresh material. While initial rates of carbonylation are slower for the regenerated catalyst, the total yield of ethyl nonanoates over 4 cycles is actually higher for the regenerated catalyst (159 mole per gram atom Pd versus 132 for fresh material). Furthermore, the average selectivity to the desired linear ethyl nonanoate is higher for the regenerated catalyst (85.2%) than for the fresh material (79.1%). After the second regeneration by acid treatment, the catalyst is less active, but the selectivity to linear ester is maintained.

EXAMPLE 5

PALLADIUM CATALYST REGENERATION VIA MINERAL ACID TREATMENT

A sample of the $10[(C_2H_5)_4N][SnCl_3]-PdCl_2[P(C_6H_5)_3]_2$ catalyst is subject to a 14 cycle carbonylation experiment similar to that described in Example 4. The catalyst recycle and regeneration procedure is similar to Example 4, the only differences of substance are that during the regeneration of the catalyst:

a. Triphenylphosphine is added in the proportion of 1 mole per mole of Pd.

b. The regenerated material is refluxed with 1-octene/ethanol for 1–2 hours under nitrogen, rather than being solvent washed.

A summary of the results is shown in Table 4.

TABLE 4
PALLADIUM CATALYST REGENERATION VIA MINERAL ACID TREATMENT - ETHYL NONANOATE SYNTHESIS[a]

| Cycle | Octene Conv(%) | Ester Linearity (Mole%) | Ethyl Nonanoate Yield(Mole%) By G.C. | Ethyl Nonanoate Yield(Mole%) Isolated | Isolated Ester Purity (%) | Total Liquid Yield (%) |
|---|---|---|---|---|---|---|
| I | 80 | 61.0 | 84 | 54 | 99 | 72 |
| II | 83 | 75.9 | 88 | 80 | 99 | 103 |
| III | 60 | 89.6 | 69 | 57 | 99 | 100 |
| IV | 43 | 90.0 | 52 | 45 | 89 | 96 |
| V | 27 | 91.2 | 31 | 23 | 99 | 100 |
| VI | 14 | 92.0 | 14 | 11 | 99 | 100 |
| VII | 68 | 82.5 | 57 | 47 | 99 | 93 |
| VIII | 21 | 84.2 | 22 | 18 | 99 | 96 |
| IX | 12 | 89.4 | 5.9 | 3.7 | 97 | 88 |
| X | 69 | 84.4 | 64 | 50 | 99 | 82 |
| XI | 32 | 85.6 | 48 | 35 | 99 | 95 |
| XII | 5 | 86.0 | 1 | 5.2 | 99 | 100 |
| XIII | 34 | 84.8 | 32 | 21 | 99 | 93 |
| XIV | 5 | 82.1 | 2.4 | 4.7 | 98 | 99 |

[a]Run Conditions: 85°, 1500 psig, CO; 4–8 hr., initial [1-octene]/[Pd]=63, [Sn]/[Pd]=10, [ethanol]/[1-octene]=1.

EXAMPLES 6–12

PALLADIUM CATALYST REGENERATION-EFFECT OF CATALYST COMPOSITION

In these examples the carbonylation of 1-octene, ethanol samples are carried out in accordance with the procedure outlined in Examples 4 and 5, but in the presence of various other ligand-stabilized palladium-(II) halide complexes dispersed in quaternary ammonium, phosphonium and arsonium salts of trihalostannate(II) and trihalogermanate(II). The following catalyst compositions showed satisfactory performance for ethyl nonanoate synthesis over 8 cycles:

$10[(C_2H_5)_4N][SnCl_3]-PdCl_2[P(p-CH_3C_6H_4)_3]_2$ $5[ClCH_2(C_6H_5)_3P][SnCl_3]-PdCl_2[P(C_6H_5)_3]_2$ $10[(n-C_4H_9)_4N][SnCl_3]-PdCl_2[P(C_6H_5)_3]_2$ $10[(C_6H_5)_4As][SnCl_3]-PdCl_2[P(C_6H_5)_3]_2$ $5[(C_2H_5)_4N][GeCl_3]-PdCl_2[P(C_6H_5)_3]_2$ $10[(C_2H_5)_4N][SnCl_3]-PdCl_2[P(p-CH_3O.C_6H_4)_3]_2$ $5[(C_7H_{15})_4N][SnCl_3]-PdCl_2[As(C_6H_5)_3]_2$

EXAMPLES 13–16

PALLADIUM CATALYST REGENERATION — EFFECT OF CHANGES IN REACTANTS

In these examples, the carbonylation of samples of equimolar α-olefin-alkanol mixtures are carried out in accordance with the procedures outlined in Examples 1, 2 and 4 using the same dispersions of palladium complex in quaternary salt, viz.

$10[(C_2H_5)_4N][SnCl_3]-PdCl_2[P(C_6H_5)_3]_2$

The following olefin-alkanol mixtures gave good yields of the corresponding esters over 8 catalyst cycles:

| | | |
|---|---|---|
| Propylene | - | 1-decanol |
| 1-hexene | - | iso-propanol |
| 1-decene | - | 2-chloroethanol |
| 1-tetradecene | - | methanol |

D. REGENERATION OF PLATINUM HYDROFORMYLATION CATALYSTS

Bis(triphenylphosphine)platinum(II) chloride and related ligand-stabilized platinum(II) halide complexes, dispersed in quaternary ammonium, phosphonium and arsonium salts of trichlorostannate(II) and trihalogermanate(II) salts have been found to be excellent catalysts for the selective hydroformylation of olefins, particularly 1-olefins, to predominantly linear aldehyde derivatives. The product aldehyde may be recovered from the platinum catalyst by distillation or solvent extraction techniques, similar to those outlined in Examples 1 and 2 of this application. After multiple cycling, the platinum catalyst may be regenerated by treatment with mineral acids.

EXAMPLE 17

PLATINUM CATALYST REGENERATION VIA MINERAL ACID TREATMENT

A sample of tetraethylammonium trichlorostannate (II) (40 mmole) and bis(triphenylphosphine)-platinum(II) chloride (4.0 mmole) are placed in a glass-lined, 300 ml. autoclave reactor, the reactor sealed, purged with CO, and pressured to 1260 psig with 42 g of propylene (1 mole) plus a 1:1 (V/V) gas mixture of $CO/H_2$. The mixture is heated to 80° C, stirred for 5 hours at temperature, and allowed to cool. Forty grams of yellow liquid product are recovered by decantation from the yellow crystalline melt, and fractionally distilled. Butyraldehydes (34.5 g. 0.48 mole) are recovered from a fraction boiling 72°–75° C (1 atm), and identified by nmr, ir, glpc and elemental analyses.

The recovered solid platinum catalyst is returned to the reactor, the reactor purged with CO, and pressured to 1260 psig with a second 42 g batch of propylene (1 mole) plus 1:1 (V/V) $CO/H_2$. Hydroformylation is carried out as described supra, and the butyraldehyde recovered by atmospheric distillation. After 3 cycles, the platinum catalyst is regenerated by mineral acid treatment as follows:

a. The solid catalyst is treated with 50–100 ml. of mineral acid consisting of a 1:1 (V/V) conc hydrochloric acid (specific gravity 1.19 at 20° C) and nitric acid (specific gravity 1.42 at 20° C).

b. The mixture of solid catalyst plus acid is evaporated to a solid at 50°–110° C.

c. Additional stabilizing ligand, such as triphenylphosphine, is added to the recovered solid catalyst from step (b) in the proportion of 2 mole of ligand per mole of platinum.

d. The regenerated catalyst is refluxed with carbon tetrachloride (100 ml.) for 1–2 hours under nitrogen, the excess liquid recovered by distillation, and the solid catalyst dried in vacuo.

EXAMPLES 18–24

PLATINUM CATALYST REGENERATION — EFFECT OF CATALYST COMPOSITION

In these examples, the hydroformylation of propene to butyraldehydes is carried out in accordance with the procedure outlined in Example 17, but in the presence of various other platinum(II) halide complexes dispersed in tetraethylammonium trichlorostannate(II). The following platinum salts showed satisfactory performance for butyraldehydes synthesis over 6 cycles.

$PtCl_2[As(C_6H_5)_3]_2$ $PtCl_2[S(C_6H_5)_2]_2$ $PtCl_2[P(OC_6H_5)_3]_2$ $PtCl_2[P(n-C_4H_9)_3]_2$ $PtCl_2[(C_6H_5)_2AsCH_2CH_2As(C_6H_5)_2]$ $PtCl_2[O-Phenanthroline]$ $PtCl_2$ As the previous Tables and Discussions have indicated the catalyst regeneration procedures of this invention are both novel and useful. They may be applied to catalysts consisting of dispersions of palladium and platinum salts in quaternary ammonium, phosphonium and arsonium salts of trihalostannate(II) and trihalogermanate(II) useful in the catalytic carbonylation, hydroformylation and hydrogenation of olefins.

Further, the invention processes are flexible in permitting changes and modifications to be made without departing from the inventive process.

However, the metes and bounds of this invention can best be gleaned by reading the claims that follow in conjunction with the rest of the specification.

What is claimed is:

1. A process for the regeneration of dispersions of spent ligand-stabilized palladium(II) or platinum(II) halide catalysts in quaternary ammonium, phosphonium and arsonium salts of trihalostannate(II) and trihalogermanate(II), the spent catalysts being obtained from the carbonylation or hydroformylation of olefins, said ligand-stabilized groups being selected from the group consisting of $P(C_6H_5)_3$, $P(p-CH_3.C_6H_4)_3$, $P(C_6H_5)_3CH_2Cl$, $As(C_6H_5)_3$, $S(C_6H_5)_2$, $P(OC_6H_5)_3$, $P(n-C_4H_9)_3$, $(C_6H_5)_2AsCH_2CH_2As(C_6H_5)_2$, the process consisting essentially of:

a. contacting each part by weight of said dispersions to be regenerated with from 0.1 part by weight to $10^3$ part by weight of mineral acid consisting of mixtures of hydrochloric acid, having a specific gravity of from 1.00 to 1.20 at 20° C, and nitric acid having a specific gravity of from 1.00 to 1.51 at 20° C, said acids being in volume ratios ranging from 0.01 to 100 parts by volume of hydrochloric acid for each part by volume of nitric acid;

b. evaporating said mixture of solid catalyst plus acid to dryness at 50°–110° C;

c. adding additional stabilizing ligand in the ratio of 1–10 mole of ligand per mile of palladium or platinum present in said spent dispersions, d. refluxing the mixture from (c) with excess organic solvent mixture, removing excess solvent and drying the dispersion to a solid in a vacuum.

2. A process for regenerating dispersions of spent ligand-stabilized palladium(II) and platinum(II) halide complexes in quaternary ammonium, phosphonium and arsonium salts of trihalostannate(II) or trihalogermanate(II) by ligand-stabilized palladium(II) and platinum(II), said ligand-stabilized catalyst being obtained from the carbonylation or hydroformylation of olefins, said ligand-stabilized dispersion to be regenerated selected from the group consisting of:

$[(C_2H_5)_4N][SnCl_3]-PdCl_2[P(C_6H_5)_3]_2$ $[(C_2H_5)_4N][SnCl_3]-PdCl_2[P(p-CH_3.C_6H_4)_3]_2$ $[ClCH_2(C_6H_5)_3P][SnCl_3]-PdCl_2[P(C_6H_5)_3]_2$ $[(n-C_4H_9)_4N][SnCl_3]-PdCl_2[P(C_6H_5)_3]_2$ $[(C_2H_5)_4N][GeCl_3]-PdCl_2[P(C_6H_5)_3]_2$ $[(C_2H_5)_4N][SnCl_3]-PdCl_2[P(p-CH_3O.C_6H_4)_3]_2$ and $[(C_7H_{15})_4N][GeCl_3]-PdCl_2[As(C_6H_5)_3]_2$ $[(C_2H_5)_4N][SnCl_3]-PtCl_2[P(C_6H_5)_3]_2$ $[(C_2H_5)_4N][SnCl_3]-PtCl_2[As(C_6H_5)_3]_2$ $[(C_2H_5)_4N][SnCl_3]-PtCl_2[S(C_6H_5)_2]_2$ $[(C_2H_5)_4N][SnCl_3]-PtCl_2[P(OC_6H_5)_3]_2$ $[(C_2H_5)_4N][SnCl_3]-PtCl_2[P(n-C_4H_9)_3]_2$ $[(C_2H_5)_4N][SnCl_3]-PtCl_2[(C_6H_5)_2AsCH_2CH_2As(C_6H_5)_2]$ $[(C_2H_5)_4N][SnCl_3]-PtCl_2[O-Phenanthroline]$ and $[(C_2H_5)_4N][SnCl_3]-PtCl_2$, $[(C_6H_5)_4As][SnCl_3]-PdCl_2[P(C_6H_5)_3]_2$ by the process consisting essentially of:
 a. contacting each part by weight of said dispersions to be regenerated with from 0.1 part by weight to $10^3$ part by weight of mineral acid concisting of mixtures of hydrochloric acid, having a specific gravity of from 1.00 to 1.20 at 20° C, and nitric acid having a specific gravity of from 1.00 to 1.51 at 20° C, said acids being in volume ratios ranging from 0.01 to 100 parts by volume of hydrochloric acid for each part by volume of nitric acid;
 b. evaporating said mixture of solid catalyst plus acid to dryness at 50°–110° C;
 c. adding additional stabilized ligand corresponding to the original ligand contained in the dispersion of spent catalyst prior to the catalyst's use in the aforementioned hydroformylation, hydrogenation and carbonylation reactions, said ligand's ratio of 1–10 moles of ligand per mole of palladium or platinum present in the spent dispersion;
 d. refluxing the mixture from (c) with excess organic solvent mixture, removing excess solvent and drying the dispersion to a solid in a vacuum.

3. A process for regenerating dispersions of $[(C_2H_5)_4N][SnCl_3]-PdCl_2[P(C_6H_5)_3]_2$ catalyst spent in carbonylating olefins, the process consisting essentially of:
 a. contacting each part by weight of said dispersions to be regenerated with from 0.1 part by weight to $10^3$ part by weight of mineral acid consisting of mixtures of hydrochloric acid, having a specific gravity of from 1.00 to 1.20 at 20° C, and nitric acid having a specific gravity of from 1.00 to 1.51 at 20° C, said acids being in volume ratios ranging from 0.01 to 100 parts by volume of hydrochloric acid for each part by volume of nitric acid;
 b. evaporating said mixture of solid catalyst plus acid to dryness at 50°–110° C;
 c. adding additional $P(C_6H_5)_3$ ligand in the ratio of 1–10 mole of ligand per mole of palladium or platinum present in said spent dispersions;
 d. refluxing the mixture from (c) with excess organic solvent mixture, removing excess solvent and drying the dispersion to a solid in a vacuum.

* * * * *